US012718942B2

(12) United States Patent
Agnello et al.

(10) Patent No.: US 12,718,942 B2

(45) **Date of Patent: *Aug. 25, 2026**

(54) CONTEXT-BASED USER INTERFACE TO MEDICAL DATABASE

(71) Applicant: ABIOMED, Inc., Danvers, MA (US)

(72) Inventors: Alessandro Simone Agnello, Danvers, MA (US); David Weber, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/059,016

(22) Filed: Feb. 20, 2025

(65) Prior Publication Data

US 2025/0259745 A1 Aug. 14, 2025

Related U.S. Application Data

(63) Continuation of application No. 17/979,098, filed on Nov. 2, 2022, now Pat. No. 12,260,955, which is a (Continued)

(51) Int. Cl.

*G16H 40/67* (2018.01)

*G16H 10/60* (2018.01)

(Continued)

(52) U.S. Cl.

CPC ............ *G16H 40/67* (2018.01); *G16H 10/60* (2018.01); *A61B 5/0002* (2013.01); *G16H 40/20* (2018.01); *G16H 50/20* (2018.01); *G16H 80/00* (2018.01)

(58) Field of Classification Search

CPC ... G06F 3/0482; G06F 3/04842; G16H 40/67; G16H 10/60; G16H 40/63; G16H 40/00; G16H 15/00; G16H 80/00; G16H 70/20

See application file for complete search history.

(56) References Cited

U.S. PATENT DOCUMENTS 9,269,354 B2 2/2016 Gandrabur et al.

9,666,185 B2 5/2017 Goussard et al.

(Continued)

FOREIGN PATENT DOCUMENTS

CN 108491312 A 9/2018

JP 2003122856 A 4/2003

(Continued)

OTHER PUBLICATIONS

Examination Report No. 1 issued in corresponding Australian Patent Application No. 2020299594, mailed Jan. 30, 2025, 3 pages.

(Continued)

*Primary Examiner* — Joseph D Burgess

(74) *Attorney, Agent, or Firm* — Botos Churchill IP Law LLP

(57) ABSTRACT

A user interface to a medical database stores context information from previous queries and uses the context information as part of information selection criteria for a current query, without requiring the users to fully specify the information selection criteria in each query. The context information is automatically stored as a profile for each user, for each group of users and, optionally, for each institution to which a user is affiliated. In response to a current user query, a combination of the information selection criterion currently entered by the user and one or more information selection criteria previously entered by the user, group and (optionally) institution is used to query the medical database. Optionally, a user's group membership may be automatically determined, based on current physical location of the user and potential groups, for example as estimated from a meeting calendar or signals received by a wireless access point.

19 Claims, 8 Drawing Sheets

Related U.S. Application Data continuation of application No. 16/458,093, filed on Jun. 30, 2019, now Pat. No. 11,527,322.

(51) Int. Cl.

| | |
|---|---|
| *A61B 5/00* | (2006.01) |
| *G16H 40/20* | (2018.01) |
| *G16H 50/20* | (2018.01) |
| *G16H 80/00* | (2018.01) |

(56) References Cited

U.S. PATENT DOCUMENTS

| | | | | |
|---|---|---|---|---|
| 2003/0036927 | A1 | 2/2003 | Bowen | |
| 2009/0125333 | A1 | 5/2009 | Heywood et al. | |
| 2010/0179819 | A1 | 7/2010 | Herbst et al. | |
| 2011/0246487 | A1 | 10/2011 | Malec et al. | |
| 2012/0136865 | A1 | 5/2012 | Blom et al. | |
| 2016/0078104 | A1 * | 3/2016 | Clifford | G06F 3/0482 707/722 |
| 2017/0032145 | A1 | 2/2017 | New et al. | |
| 2017/0161439 | A1 | 6/2017 | Raduchel et al. | |
| 2019/0188410 | A1 | 6/2019 | Briscoe et al. | |
| 2020/0179819 | A1 | 6/2020 | Vucinovic | |

FOREIGN PATENT DOCUMENTS

| | | | |
|---|---|---|---|
| JP | 2005310094 | A | 11/2005 |
| JP | 2010244187 | A | 10/2010 |
| JP | 2011028730 | A | 2/2011 |
| JP | 2012113603 | A | 6/2012 |
| JP | 2014006644 | A | 1/2014 |
| JP | 2017016355 | A | 1/2017 |

OTHER PUBLICATIONS

European Patent Office, International Search Report and Written Opinion for PCT application No. PCT/US20/37686, Sep. 9, 2020 (14 pages).

Nuance Communications, Inc., Recognizing the power of speech, Nuance Recognizer Data Sheet, Recognizer 10.5, Jun. 5, 2015 (2 pages).

Nuance Communications, Inc., Recognizing the power of speech, Nuance Recognizer Data Sheet, Recognizer 11, Jan. 4, 2018 (2 pages).

Office Action from corresponding European Patent Application No. 20 735 784.9 dated Dec. 3, 2024 (4 pp.).

Office Action from corresponding Japanese Patent Application No. 2021577892 dated Jul. 9, 2024 (6 pp.).

Office Action issued in corresponding Indian Patent Application No. 202217002838 dated Feb. 1, 2023 (6 pp.).

""Smart fuzzy querying based on user's profile and context: A critical care planning system case study,"", F. Saidi and J. Akaichi, 2015 5th National Symposium on Information Technology: Towards New Smart World (NSITNSW), 2015, pp. 1-7, doi: 10.1109/NSITNSW.2015.7176404. (Year: 2015).

Office Action from corresponding Japanese Patent Application No. 2025-046313 dated Mar. 24, 2026 (6 pp.).

Office Action issued in Chinese Patent Application No. 202080056209.3 dated Apr. 27, 2026 (20 pp.).

Notice of Allowance issued in Korean Patent Application No. 10-2022-7003547, dated Jun. 26, 2026 (8 pp.).

* cited by examiner

CONTEXT-BASED USER INTERFACE TO MEDICAL DATABASE

CROSS-REFERENCE TO RELATED APPLICATIONS

This application is a continuation of U.S. application Ser. No. 17/979,098, filed on Nov. 2, 2022, issued as U.S. Pat. No. 12,260,955, which is a continuation of U.S. application Ser. No. 16/458,093, filed on Jun. 30, 2019, issued as U.S. Pat. No. 11,527,322, the disclosures of which are incorporated herein by reference.

BACKGROUND

The present invention relates to user interfaces to databases and, more particularly, to user interfaces to medical databases, in which information selection criteria from previous queries are used in a current query, without requiring a user to repeat the previous information selection criteria.

Many patients are connected to medical devices temporarily or longer. For example, heart attack victims may have heart pumps implanted temporarily to reduce loads on the patients' hearts, while the hearts recover. Heart monitors, blood pressure monitors, infusion pumps and many other types of medical devices may be connected to patients for longer terms, such as while the patients are admitted to hospitals. Remote monitoring systems, such as the Impella Connect remote monitoring system available from Abiomed, Inc., Danvers, MA, enable clinicians and others to remotely monitor such medical devices. However, with a large number of medical devices distributed across a large number of medical institutions, it is sometimes difficult for a clinician to easily specify a single medical device, patient or institution of interest, or a set of medical devices, patients and/or institutions of interest.

BRIEF SUMMARY

An embodiment of the present invention provides a medical database query system. The medical database query system is usable by a plurality of users. Each user is associated with at least one group of users.

A first database, of the medical database query system, is configured to store information about at least one of: (a) a plurality of medical devices, (b) a plurality of medical institutions and (c) a plurality of patients. Each medical device is configured for connection to a respective patient. Each medical institution is configured to admit patients and house medical devices configured for connection to respective patients. The information about the plurality of patients includes information about medical institutions, at which respective ones of the patients are currently admitted, and information about medical devices, to which respective ones of the patients are currently connected.

A human user interface is configured to receive, from a user, a series of requests. Each request includes a request for information from the database. Each request includes a respective information selection criterion.

A second database is configured to store, for each user, corresponding user profile information and, for each group of users, corresponding group profile information.

A user profiler is configured to store, in response to at least some requests of the series of requests, the information selection criterion of each such request into the second database in association with the user who made the at least some requests, thereby augmenting the user profile information for the user.

A group profiler is configured to store, in response to at least some requests of the series of requests, the information selection criterion of each such request into the second database in association with at least one group associated with the user who made the at least some requests, thereby augmenting the group profile information for the at least one group.

A database query engine is configured to search the first database. The search is based on a combination of: (a) an information selection criterion from a current request of the series of requests, (b) at least one information selection criterion from the user profile information corresponding to the user who made the current request and (c) at least one information selection criterion from the group profile information corresponding to a group associated with the user who made the current request.

A database response engine is configured to provide to the user a result returned by the database query engine.

Optionally, in any embodiment, each user may be associated with an institution. In such an embodiment, the second database is further configured to store, for each institution, corresponding institution profile information. Such an embodiment also includes an institution profiler. The institution profiler is configured to store, in response to at least some requests of the series of requests, the information selection criterion of each such request into the second database in association with the institution associated with the user who made the at least some requests, thereby augmenting the institution profile information for the institution. In this embodiment, the combination, upon which the database query engine is configured to search the first database, includes: (d) at least one information selection criterion from the institution profile information corresponding to an institution associated with the user who made the current request.

Optionally, any embodiment may include a user logon module configured to automatically identify the user, based on the respective information selection criteria of a subset of the series of requests.

Optionally, in any embodiment with a user logon module, the user logon module may be further configured to automatically identify the group associated with the user, based on the respective information selection criteria of a subset of the series of requests.

Optionally, in any embodiment with a user logon module, the user logon module may be further configured to automatically identify the institution associated with the user, based on the respective information selection criteria of a subset of the series of requests.

Optionally, in any embodiment with a user logon module, the user logon module may be further configured to automatically query a third database. The third database may be configured to store information about a plurality of users including, for each user, an estimated current location of the user. The third database may be further configured to store information about a plurality of groups of users including, for each group, an estimated current location of the group. The user logon module may be further configured to automatically compare the estimated current location of the user to the estimated current location of at least one group of the plurality of groups and identify the group associated with the user, based on a match between the estimated current location of the user and the estimated current location of the at least one group of the plurality of groups.

Optionally, in any embodiment with a third database, the third database may include a calendar database configured to store information about a plurality of meetings including, for each meeting, a location of the meeting, a time of the meeting and a list of participants in the meeting.

Optionally, in any embodiment with a user logon module, in order to identify the group associated with the user, the user logon module may be configured to automatically parse a title of a current meeting, of the plurality of meetings, in which the user is a participant.

Optionally, in any embodiment with a user logon module, in order to identify the group associated with the user, the user logon module may be configured to automatically identify at least one participant, other than the user, among the list of participants in a current meeting, of the plurality of meetings, in which the user is also a participant.

Optionally, in any embodiment with a third database, the third database may include an electronic mail database configured to store a plurality of electronic messages including, for each electronic message, a subject and a list of recipients of the electronic message.

Optionally, in any embodiment with a user logon module, in order to identify the group associated with the user, the user logon module may be configured to automatically parse a distribution list of an electronic message of the plurality of electronic messages.

Optionally, in any embodiment with a user logon module, in order to identify the group associated with the user, the user logon module may be configured to automatically parse a subject of an electronic message of the plurality of electronic messages.

Optionally, in any embodiment with a user logon module, in order to identify the group associated with the user, the user logon module may be configured to automatically identify at least one recipient among the list of recipients of an electronic message of the plurality of electronic messages.

Optionally, in any embodiment with a third database, the third database may be configured to store the estimated current location of the user, based on information from a wireless access point to which a wireless mobile device, that is registered to the user, is currently wirelessly connected.

Optionally, in any embodiment with a third database, the third database may be configured to store the estimated current location of the user, based on information from a wireless access point to which a wireless mobile device, that is registered to the user, is currently wirelessly connected, and store the estimated current location of the group, based on information from at least one wireless access point to which respective wireless mobile devices, that are registered to the respective users associated with the group, are currently wirelessly connected.

Optionally, in any embodiment, the human user interface may include a speech user interface and/or a graphical user interface and/or a text user interface.

Another embodiment of the present invention provides a method for querying a medical database. The medical database is accessible by a plurality of users. The method is usable by a plurality of users. Each user is associated with at least one group of users.

A first database is provided. The first database is configured to store information about at least one of: (a) a plurality of medical devices, (b) a plurality of medical institutions, and (c) a plurality of patients. Each medical device is configured for connection to a respective patient. Each medical institution is configured to admit patients and house medical devices configured for connection to respective patients. The information about the plurality of patients includes information about medical institutions, at which respective ones of the patients are currently admitted, and information about medical devices, to which respective ones of the patients are currently connected.

A series of requests is received from a user, via a human user interface. Each request includes a request for information from the database. Each request includes a respective information selection criterion.

A second database is provided. The second database is configured to store, for each user, corresponding user profile information and, for each group of users, corresponding group profile information.

In response to at least some requests of the series of requests, the information selection criterion of each such request is stored into the second database, in association with the user who made the at least some requests, thereby augmenting the user profile information for the user.

In response to at least some requests of the series of requests, the information selection criterion of each such request is stored into the second database, in association with at least one group associated with the user who made the at least some requests, thereby augmenting the group profile information for the at least one group.

The first database is searched, based on a combination of: (a) an information selection criterion from a current request of the series of requests, (b) at least one information selection criterion from the user profile information corresponding to the user who made the current request and (c) at least one information selection criterion from the group profile information corresponding to a group associated with the user who made the current request.

A result returned, as a result the searching of the first database, is provided to the user.

Optionally, in any embodiment, each user may be associated with an institution. In such an embodiment, the second database is further configured to store, for each institution, corresponding institution profile information. In such an embodiment, in response to at least some requests of the series of requests, the information selection criterion of each request is stored into the second database, in association with the institution associated with the user who made the at least some requests, thereby augmenting the institution profile information for the institution. In addition, the combination, upon which the first database is searched, includes: (d) at least one information selection criterion from the institution profile information corresponding to an institution associated with the user who made the current request.

Optionally, in any embodiment, the user may be automatically identified, based on the respective information selection criteria of a subset of the series of requests.

Optionally, in any embodiment, the group associated with the user may be automatically identified, based on the respective information selection criteria of a subset of the series of requests.

Optionally, in any embodiment, the institution associated with the user may be automatically identified, based on the respective information selection criteria of a subset of the series of requests.

Optionally, in any embodiment, a third database may be queried. The third database may be configured to store information about a plurality of users and a plurality of groups of users. The information about the plurality of users includes, for each user, an estimated current location of the user. The information about the plurality of groups of users includes, for each group, an estimated current location of the group. The estimated current location of the user may be compared to the estimated current location of at least one group of the plurality of groups. The group associated with the user may be identified, based at least in part on a match between the estimated current location of the user and the estimated current location of the at least one group of the plurality of groups.

Optionally, in any embodiment with a third database, the third database may include a calendar database configured to store information about a plurality of meetings including, for each meeting, a location of the meeting, a time of the meeting and a list of participants in the meeting.

Optionally, in any embodiment, identifying the group associated with the user may include automatically parsing a title of a current meeting, of the plurality of meetings, in which the user is a participant.

Optionally, in any embodiment, identifying the group associated with the user may include automatically identify at least one participant, other than the user, among the list of participants in a current meeting, of the plurality of meetings, in which the user is also a participant.

Optionally, in any embodiment with a third database, the third database may include an electronic mail database configured to store a plurality of electronic messages including, for each electronic message, a subject and a list of recipients of the electronic message.

Optionally, in any embodiment, identifying the group associated with the user may include automatically parsing a distribution list of an electronic message of the plurality of electronic messages.

Optionally, in any embodiment, identifying the group associated with the user may include automatically parsing a subject of an electronic message of the plurality of electronic messages.

Optionally, in any embodiment, identifying the group associated with the user may include identifying at least one recipient among the list of recipients of an electronic message of the plurality of electronic messages.

Optionally, in any embodiment with a third database, the third database may be configured to store the estimated current location of the user, based on information from a wireless access point to which a wireless mobile device, that is registered to the user, is currently wirelessly connected.

Optionally, in any embodiment with a third database, the third database may be configured to store the estimated current location of the user and the estimated current location of the group. The estimated current location of the user may be based on information from a wireless access point to which a wireless mobile device, that is registered to the user, is currently wirelessly connected. The estimated current location of the group may be based on information from at least one wireless access point to which respective wireless mobile devices, that are registered to the respective users associated with the group, are currently wirelessly connected.

Optionally, in any embodiment, the human user interface may include a speech user interface and/or a graphical user interface and/or a text user interface.

Yet another embodiment of the present invention provides a non-transitory computer-readable medium. The medium is encoded with instructions. When executed by a processor, the instructions establish processes for performing a computer-implemented method for querying a medical database usable by a plurality of users. Each user is associated with at least one group of users. The processes include the following:

A process configured to access a first database. The first database is configured to store information about at least one of: (a) a plurality of medical devices, (b) a plurality of medical institutions and (c) a plurality of patients. Each medical device is configured for connection to a respective patient. Each medical institution is configured to admit patients and house medical devices configured for connection to respective patients. The information about the plurality of patients includes information about medical institutions, at which respective ones of the patients are currently admitted, and information about medical devices, to which respective ones of the patients are currently connected.

A human user interface configured to receive, from a user, a series of requests. Each request including a request for information from the database. Each request includes a respective information selection criterion.

A second database. The second database is configured to store, for each user, corresponding user profile information and, for each group of users, corresponding group profile information.

A user profiler. The user profiler is configured to store, in response to at least some requests of the series of requests, the information selection criterion of each such request into the second database, in association with the user who made the at least some requests, thereby augmenting the user profile information for the user.

A group profiler. The group profiler is configured to store, in response to at least some requests of the series of requests, the information selection criterion of each such request into the second database, in association with at least one group associated with the user who made the at least some requests, thereby augmenting the group profile information for the at least one group.

A database query engine. The database query engine is configured to search the first database, based on a combination of: (a) an information selection criterion from a current request of the series of requests, (b) at least one information selection criterion from the user profile information corresponding to the user who made the current request and (c) at least one information selection criterion from the group profile information corresponding to a group associated with the user who made the current request.

A database response engine. The database response engine is configured to provide, to the user, a result returned by the database query engine.

BRIEF DESCRIPTION OF THE DRAWINGS

The invention will be more fully understood by referring to the following Detailed Description of Specific Embodiments in conjunction with the Drawings, of which.

DETAILED DESCRIPTION

Figure 1:
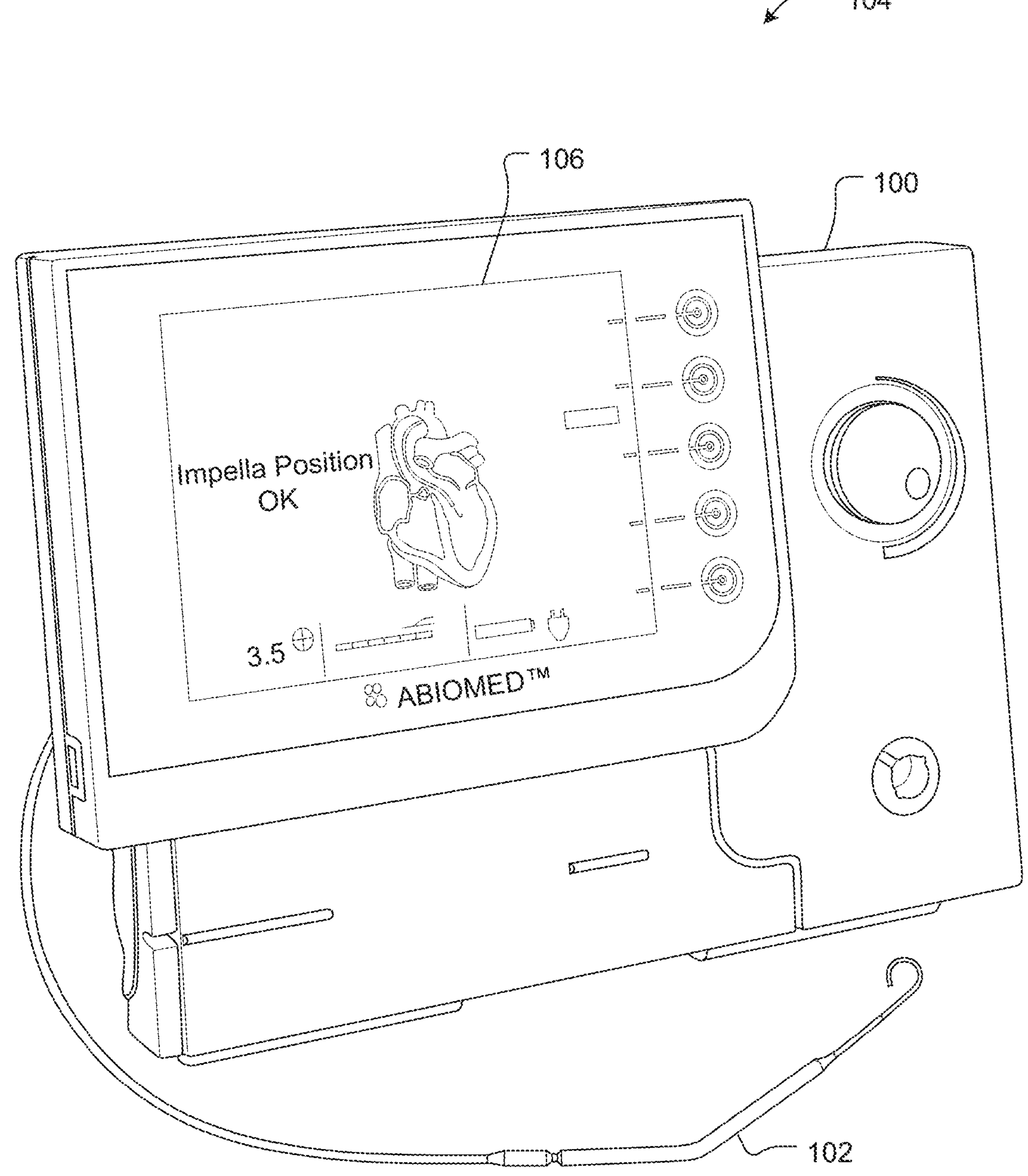
FIG. 1 is a perspective view of an exemplary convention medical device controller and an exemplary conventional medical device, in this example a heart pump, coupled to the medical device controller, according to the prior art.

Embodiments of the present invention provide user interfaces to medical databases. The user interfaces store context information from previous queries and use the context information as part of their information selection criteria for a current query, thereby easing a user's burden in specifying information the user wishes to receive, thereby freeing the user to concentrate on narrowing or otherwise clarifying the kind of information the user seeks.

Embodiments summarized above and described in further detail below have the effect of improving accuracy of database query systems in providing information requested by users, without requiring the users to fully specify the information in each query. Each user query includes at least one information selection criterion. This information selection criterion is used to select information from a database. However, these embodiments automatically create and utilize user profiles, which store information selection criteria previously entered by respective users in previous queries. In response to a current user query, embodiments combine: (a) the information selection criterion entered by the user in the current query with (b) one or more information selection criteria that were previously entered by the user, and stored in the user profile, to form more specific information selection criteria. The more specific information selection criteria are used to select information from the database. The selected information is then provided to the user. Thus, these embodiments utilize context, provided by recent queries by the user, to select the information from the database.

Each user is a member of, and is therefore associated with, at least one group. Examples of groups include: doctors caring for a particular patient; doctors affiliated with a particular medical practice or office; nurses assigned to a particular hospital floor or ward; technicians who maintain medical devices; administrators affiliated with a particular hospital; and technical support representatives affiliated with a particular medical device manufacturer. These embodiments also automatically create and utilize group profiles, which store information selection criteria entered in previous queries by users of the respective groups. In response to a current user query, embodiments combine: (a) the information selection criterion entered by the user in the current query with (b) one or more information selection criteria that were previously entered by the user, and stored in the user profile, and (c) one or more information selection criteria that were previously entered by users in the same group as the user, and stored in the group profile, to form more the specific information selection criteria.

Optionally, each user is associated with an institution, for example a hospital that employs the user or that has granted admitting privileges to the user. Other examples of institutions include manufacturers of medical devices and research organizations, such as universities. Some embodiments automatically create and utilize institution profiles, which store information selection criteria entered in previous queries by users associated with the respective institutions. In response to a current user query, these embodiments combine: (a) the information selection criterion entered by the user in the current query with (b) one or more information selection criteria that were previously entered by the user, and stored in the user profile, (c) one or more information selection criteria that were previously entered by users in the same group as the user, and stored in the group profile, and (d) one or more information selection criteria that were previously entered by users associated with the same institution as the user, and stored in the institution profile, to form the more specific information selection criteria.

Thus, these and other embodiments provide database information that more accurately meets the needs of the users, without burdening the users with fully specifying each query. These embodiments are premised on an assumption that a human user typically does not initially know how to fully specify a query and, instead, performs a series of progressively narrower queries, a series of progressively broader queries or a series of queries having an ever-shifting focus, until the user has refined his query to meet his needs. Often, the user does not know, a priori, what information he needs and, instead, essentially experiments with his queries until he is presented with information that appears to be useful. Sometimes, information returned in response to a query raises a question, which causes the user to perform a different, but related, query.

These embodiments take advantage of the fact that, in a series of queries by a user, at least some information selection criteria are likely to be identical or similar among the queries. Thus, context, defined by initial queries of the series of queries, can be inferred and carried over to subsequent queries, and the user can concentrate on narrowing or broadening the scope of his query, rather than on repeating all previously-entered information selection criteria.

The group and institution profiles further ease the user's burden in specifying information the user wishes to receive, by taking advantage of similarities among likely queries by users who are members of a group and users who are associated with a common institution. Some embodiments automatically determine a user's current group membership, based on an automatically determined current physical location of the user. For example, if a user is physically located proximate a set of other users, such as in a conference room, these embodiments may estimate that the user is currently a member of a group that includes the other users in the conference room. The user's current physical location may be estimated by these embodiments from a meeting calendar, signals received by a wireless access point from the user's mobile device, ex. telephone, tablet or lap top computer, or other available information.

FIG. 1 is a perspective view of an exemplary convention medical device controller 100 and an exemplary conventional implantable medical unit 102, in this example a heart pump, coupled to the medical device controller 100. In the example shown in FIG. 1, the medical device controller 100 is an Automated Impella Controller® from Abiomed, Inc., Danvers, MA, and the heart pump 102 is an Impella® 2.5 heart pump, also available from Abiomed, Inc., although any suitable medical unit and controller may be used.

The medical unit is connectable to a patient, such as by implanting the medical unit into the patient or by connecting the medical unit to the patient, such as via wires, straps, optical beams, etc. For example, an automated blood pressure cuff (not shown) is a medical unit that may be connected to a patient via a strap. In another example, an electrocardiograph (not shown) is a medical unit that may be connected to a patient via electrical wires.

Collectively, the medical device controller 100 and any associated medical unit are referred to herein as a medical device 104. In some cases, the medical unit and its associated medical device controller are combined. Such a combination is also referred to herein simply as a medical device 104.

Figure 2:
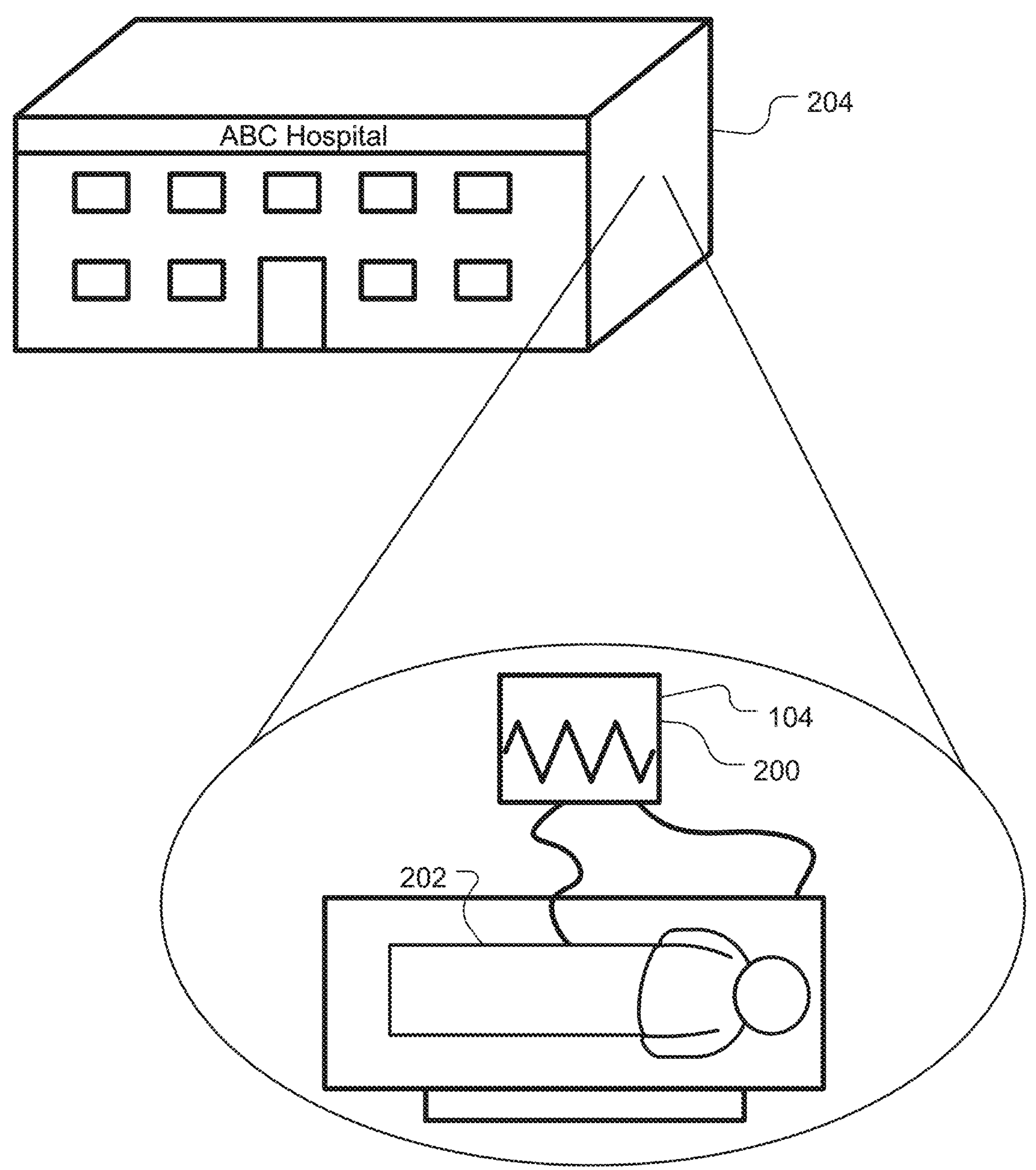
FIG. 2 is an illustration of an exemplary patient connected to an exemplary medical device, in this example a heart monitor, and admitted to an exemplary medical institution, in the context of an embodiment of the present invention.

As illustrated in FIG. 2, each medical device 104, in this case a heart monitor 200, is configured for connection to a respective patient 202. Medical institutions 204, here represented by a hospital, are configured to admit patients, such as the patient 202, and to house medical devices 104, such as the heart monitor 200. Other examples of medical institutions 204 include clinics, doctor offices, medical research facilities and medical device manufacturers.

Returning to FIG. 1, the medical device controller 100 may include a display screen 106, on which the medical device controller 100 displays operational data about the medical unit 102, such as heart signal level, battery temperature, blood flow rate and plumbing integrity. The medical device controller 100 may be connected to a computer network and thereby send the operational data to a remote data server, as shown in FIG. 3.

Figure 3:
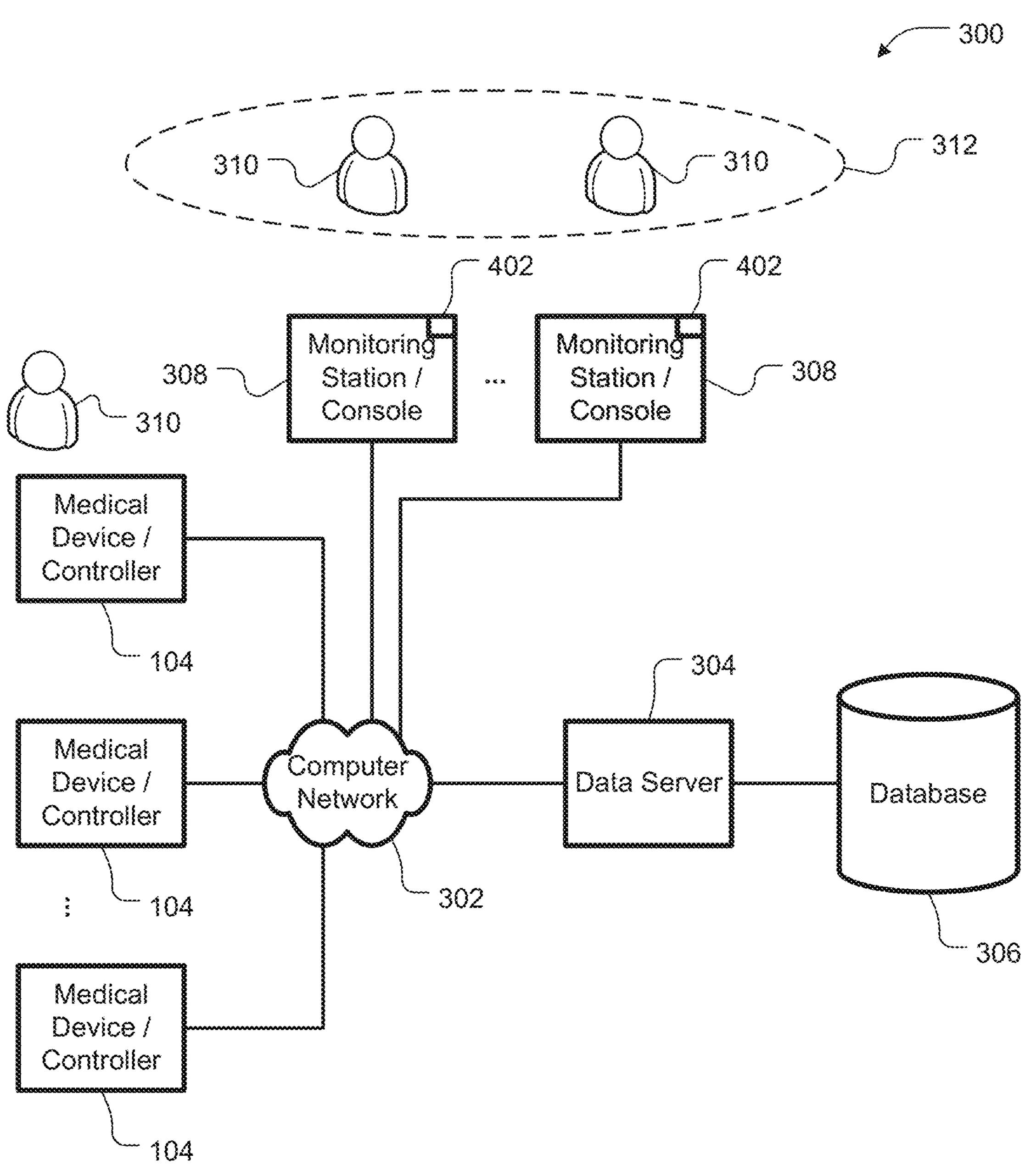
FIG. 3 is a schematic block diagram of major components of a data storage and retrieval system for collecting, storing and retrieving operational data about medical devices, patients and medical institutions, such as the medical device of FIG. 1 and the patient and medical institution of FIG. 2, in the context of an embodiment of the present invention.

FIG. 3 is a schematic block diagram of major components of a data storage and retrieval system 300 for collecting, storing and retrieving operational data from and about medical devices, represented by exemplary medical devices 104. Although three medical devices 104 are shown, other numbers of medical devices 104 may be used. The medical devices 104 may all be located at a single medical institution 204, or the medical devices 104 may be distributed over several medical institutions 204. Each medical device 104 may, but need not necessarily, be connectable to a computer network 302. Each network-connectable medical device 104 is configured to automatically repeatedly capture status information about itself 104 and send messages containing the status information via the computer network 302 to a data server 304, which stores the status information in a database 306. Monitoring stations, exemplified by monitoring stations 308, may request information, via the data server 304, from the database 306 and display this information to users, represented by users 310. An exemplary group 312 of user 310 is also shown in dotted line.

The monitoring stations 308 may also act as consoles, in which case the monitoring stations/consoles 308 may be used by the users 310 to manually enter information into the database 306. In addition, some medical devices 104 may include user interfaces, by which the users 310 can enter information, for storage in the database 306. For example, when a heart pump (FIG. 1) is implanted into a patient 202, patient information, such as name of a medical institution 204, such as a hospital, in which the patient 202 has been admitted, hospital room number, identifiers of users who are privileged to access information about the patient 202, an identification of the medical device 104 connected to the patient 202, the medical institution 204 housing the medical device 104 or into which the patient 202 has been admitted, etc. may be entered and thereby stored by the data server 304 into the database 306.

The database 306 thus stores information about the medical devices 104. Specifically, the database 306 is configured to store information about at least one of: (a) a plurality of medical devices 104, (b) a plurality of medical institutions 204 and (c) a plurality of patients 202. The information about the medical devices 104 includes information about medical institutions 204 at which respective ones of the patients 202 are currently admitted and information about medical devices 104 to which respective ones of the patients 202 are currently connected. The information about the patients 202 includes information about medical institutions 204, at which respective ones of the patients 202 are currently admitted, and information about medical devices 104, to which respective ones of the patients 202 are currently connected.

Although FIG. 3 shows a single database 306, several sub-databases may be used, such as one sub-database per medical institution 204 or per political jurisdiction, ex. Europe, Japan and the United States. Thus, for example, a separate sub-database may be used to store information about patients 202 admitted into each medical institution 204 and/or information about medical devices 104 housed at each medical institution 204. Nevertheless, collectively these sub-databases are referred to herein as the database 306.

Figure 4:
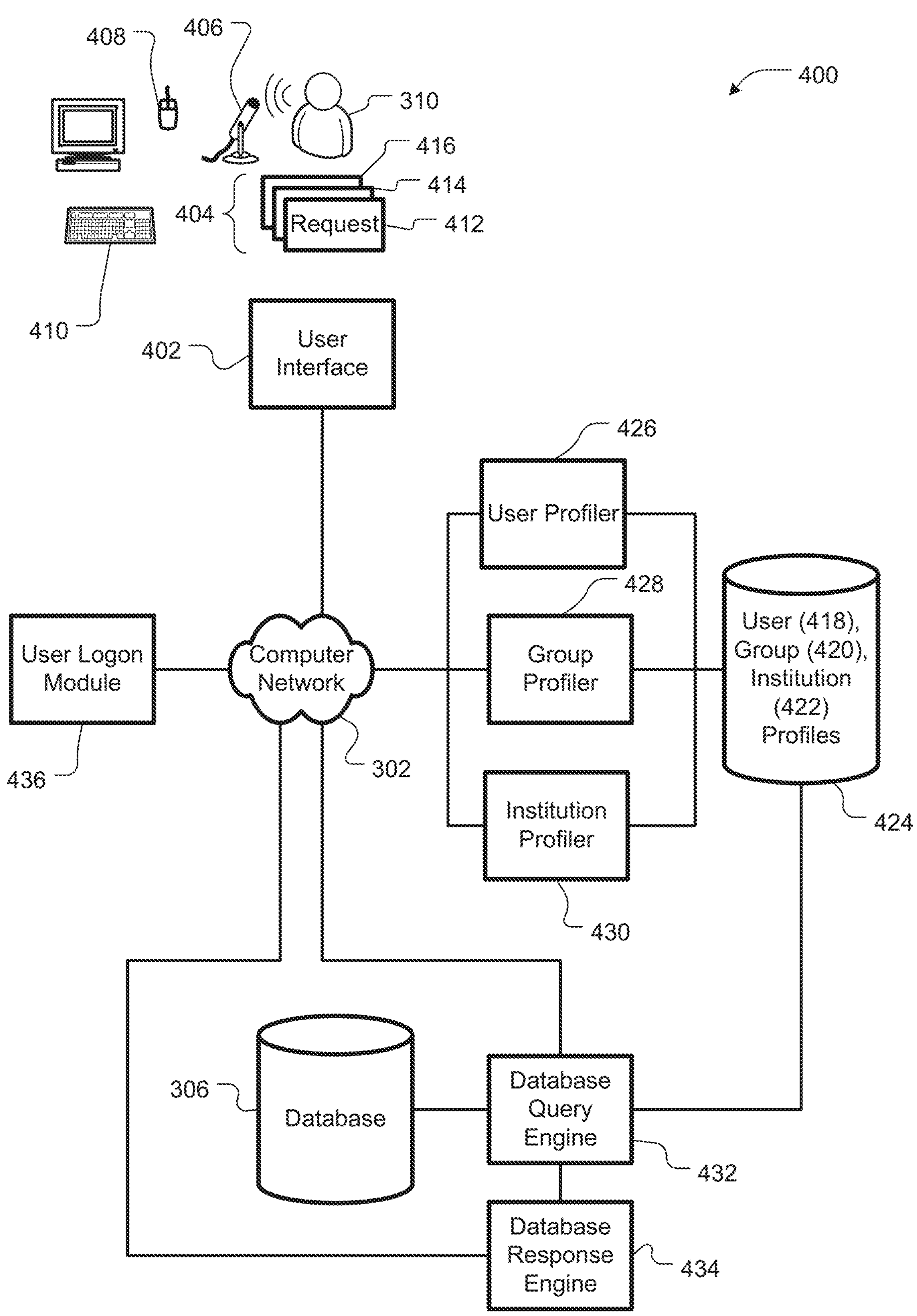
FIG. 4 is a schematic block diagram of a medical database query system, including a medical database of FIG. 3, according to an embodiment of the present invention.

FIG. 4 is a schematic block diagram of a medical database query system 400, according to an embodiment of the present invention. The medical database query system 400 includes, and queries, the database 306 shown in FIG. 3.

A human user interface 402 is configured to receive a series of requests 404 from a user 310. Although one human user interface 402 and one user 310 are shown, the medical database query system 400 may include any number of the human user interfaces 402 and may be used by any number of users 310. For example, each monitoring station/console 308 (FIG. 3) may include the human user interface 402. Returning to FIG. 4, the human user interface 402 may include any combination of: a speech user interface 406, a graphical user interface 408 and/or a text-based user interface 410.

Each request of the series of requests 404 is a request for information from the database 306. Each request of the series of requests 404 includes at least one respective information selection criterion. Examples of information selection criteria include: a selection criterion that specifies a particular patient 202, such as by medical identification number (MIN); or a particular medical institution 204, such as by name or identification number; or a particular medical device 104, such as by serial number, manufacturer, function or type. An exemplary query is, "Show me information about Impella heart pump serial number 179078."

Each request of the series of requests 404 may include a combination of information selection criteria. For example, "Show information about patient with medical identification number 123 at ABC Hospital." Although some requests specify a single patient 202, medical device 104 and/or medical institution 204, a request may specify more than one patient 202, more than one medical device 104 and/or more than one medical institution 204. For example, "Show me all heart pumps at ABC Hospital," or "Show me all heart pumps in alarm."

As a result of obtaining information about a set of patients 202, medical devices 104 and/or medical institutions 204, the user 310 may wish to narrow or refine the search. For example, after requesting the system 400 to "Show me all heart pumps at ABC Hospital," the user 310 may wish to see information about only heart pumps that are in alarm, or only heart pumps that have been implanted for more than a specified amount of time, at ABC Hospital. Thus, in a subsequent request, the user 310 may request the system 400 to "Show alarms," or "Show implants longer than two days." The medical database query system 400 uses the most recent request 412 of the series of requests 404, in the context of previous requests, such as previous requests 414 and 416, to construct selection criteria, with which to query the medical database 306 to satisfy the user's 310 current request 412. Thus, the user queries "Show alarms" and "Show implants longer than two days" may be implemented by the medical database query system 400 as "Show me all heart pumps at ABC Hospital in alarm," and "Show me all heart pumps at ABC Hospital implanted longer than two days," respectively.

The medical database query system 400 stores user profiles 418, group profiles 420 and (optionally) institutional profiles 422 in a second database 424. Each user profile 418 includes information selection criteria from some of the previous requests 414-416 made by the user 310. The second database 424 is configured to store corresponding user profile information for each user 310. Similarly, the second database 424 is configured to store corresponding group profile information for each group and (optionally) to store corresponding institutional profile information for each medical institution.

In response to the user 310 making a request 412, a user profiler 426 stores the information selection criteria (on) of the current request 412 into the second database 424 and associates the information selection criteria (on) with the user 310 who made the request 412. Thus, over time, as the user makes a series of requests 404, the user profiler 426 augments the user profile information 418 for the user 310.

Similarly, in response to the user 310, and other users, making a request 412, a group profiler 428 stores the information selection criteria (on) of the current request 412 into the second database 424 and associates the information selection criteria (on) with a group, of which the user 310 who made the request 412 is a member. Thus, over time, as the users 310 in the group 312 make requests, the group profiler 428 augments the group profile information 420 for the group.

Similarly, optionally, in response to the user 310, or other users, making a request 412, an institution profiler 430 stores the information selection criteria (on) of the current request 412 into the second database 424 and associates the information selection criteria (on) with an institution 204, to which the user 310 who made the request 412 is affiliated. Thus, over time, as the users affiliated with the institution 204 make requests, the institution profiler 430 augments the institution profile information 422 for the institution.

As noted, the medical database query system 400 uses the most recent request 412 of the series of requests 404, in the context of previous requests 414-416, to construct selection criteria, with which to query the medical database 306 to satisfy the user's 310 current request 412. A database query engine 432 is configured to search the medical database 306, based on a combination of: (a) the information selection criteria (on) from the current request 412, (b) at least one information selection criterion from the user profile information 418 corresponding to the user 310 who made the current request 412, (c) at least one information selection criterion from the group profile information 420 corresponding to a group 312 associated with the user 310 who made the current request 412 and (optionally) (d) at least one information selection criterion from the institution profile information 422 corresponding to an institution 204 associated with the user 310 who made the current request 412.

Figure 5:
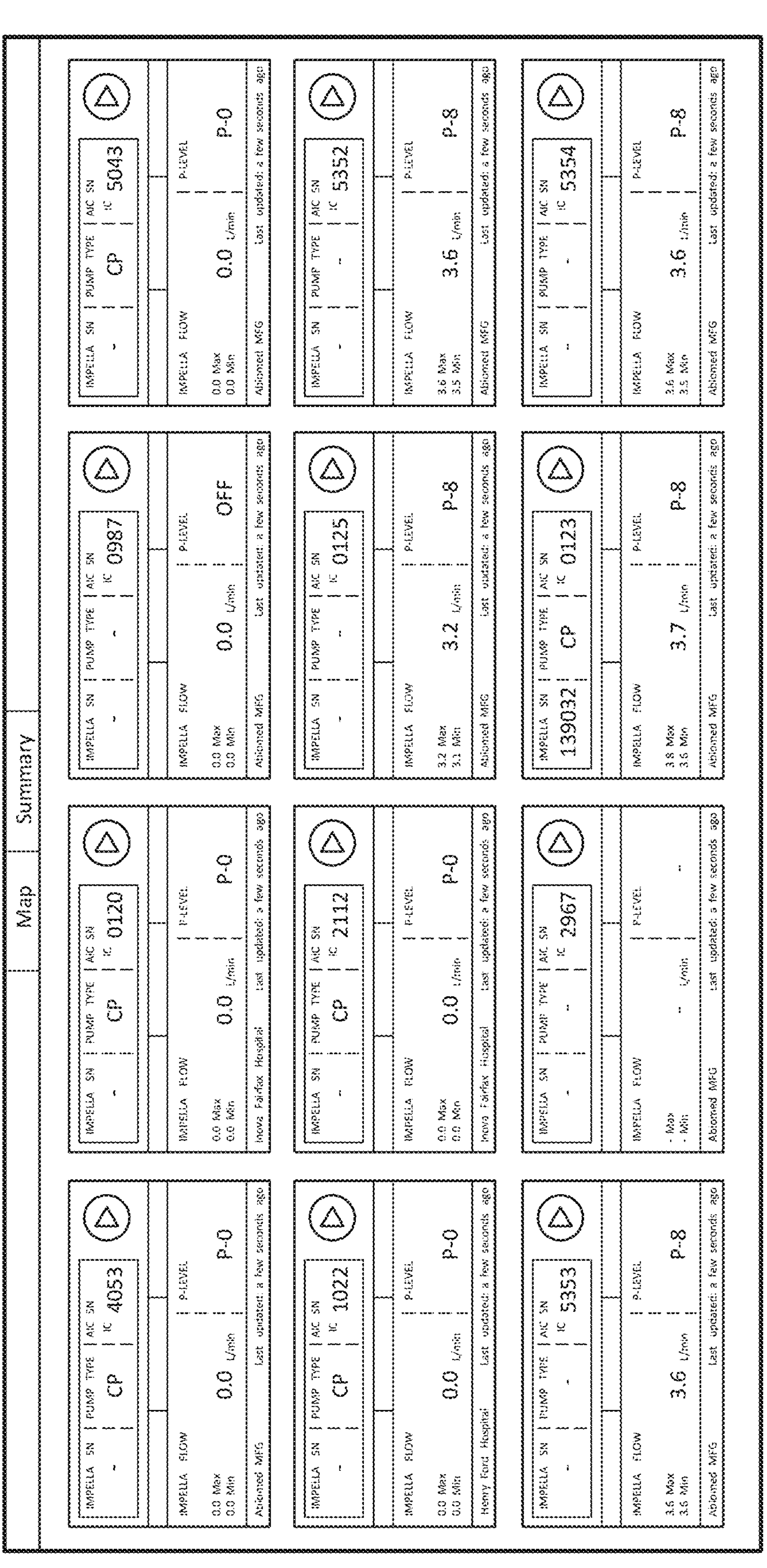
FIG. 5 illustrates exemplary hypothetical results returned by a database query engine of the medical database query system of FIG. 4 and displayed to a user, such as by a monitoring station/console of FIG. 3.

A database response engine 434 provides to the user 310 a result returned by the database query engine 432. FIG. 5 illustrates exemplary hypothetical results 500 returned by the database query engine 432 and displayed to the user 310, such as by one of the monitoring stations/consoles 308 (FIG. 3).

Each user's 310 membership in one or more groups 312 and/or affiliation with one or more institutions 204 may be represented by data stored in the database 424. This data may be entered and maintained by an administrator via an administrative user interface (not shown).

However, optionally, a user logon module 436 automatically identifies the user 310, the group 312 with which the user 310 is associated and/or the institution 204 with which the user 310 is associated, such as based on information selection criteria in a subset of the series of requests 404 made by the user 310. One method for automatically identifying the user 310 is to compare information selection criteria in the subset of requests to information selection criteria in the user profiles 418. The user profile 418 that contains information selection criteria that best match the information selection criteria in the subset of requests may be assumed to be associated with the current user 310 and, therefore, be used to identify the current user 310.

Similarly, one method for automatically identifying the group 312 of the current user 310 is to compare information selection criteria in the subset of requests to information selection criteria in the group profiles 420. The group profile 420 that contains information selection criteria that best match the information selection criteria in the subset of requests recently made by the user 310 may be assumed to be associated with the current user 310.

Similarly, one method for automatically identifying the institution 204 of the current user 310 is to compare information selection criteria in the subset of requests to information selection criteria in the institution profiles 422. The institution profile 422 that contains information selection criteria that best match the information selection criteria in the subset of requests recently made by the user 310 may be assumed to be associated with the current user 310.

Another method for automatically identifying the user 310 and/or the group 312 and/or institution 204, to which the user 310 is associated, is based on the current location of the user 310. In an embodiment, the current or estimated location of the user 310 is compared to estimated locations of several potential groups 312, and the group 312 to which the user 310 is most proximate may be assumed to be the group 312 to which the user 310 is currently associated. For example, if the user 310 is a member of several groups 312, and one of those groups 312, for example a Compliance Group or members of the Compliance Group, are currently meeting in a particular conference room, and the user 310 is scheduled to attend the meeting, the user 310 may be assumed to be meeting with the Compliance Group and, therefore, to currently be a member of that group 312. Thus, in order to identify the group 312 associated with the user 310, the user logon module 436 may automatically identify at least one participant, other than the user 310, among the list of participants in a current meeting, in which the user 310 is also a participant.

Similarly, if the user 310 is affiliated with several institutions 204, the current or estimated location of the user 310 may be compared to locations of several institutions 204, and the institution 204 to which the user 310 is most proximate may be assumed to be the institution 204 to which the user 310 is currently associated.

Figure 6:
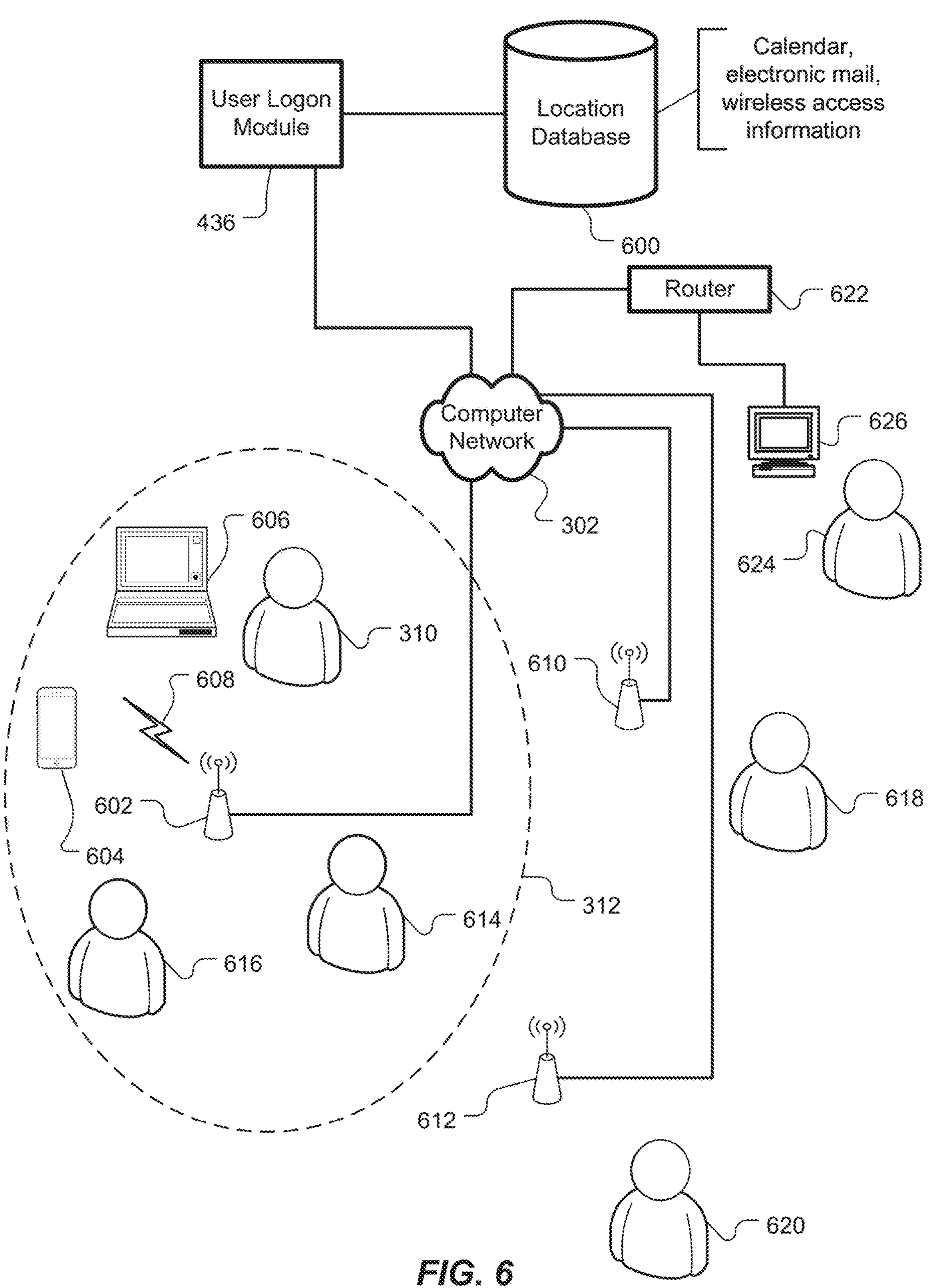
FIG. 6 is a schematic block diagram of optional components of the medical database query system of FIG. 4, including a user logon module and a location database, according to respective embodiments of the present invention.

The user logon module 436 may use a location database 600, and optionally other infrastructure, as shown schematically in FIG. 6 to automatically estimate the user's 310 current location and/or to automatically identify the group 312, in which the user 310 is currently a member. The location database 600 can, but need not, be distinct from the other databases 306 and 424. The location database 600 is configured to store information about users 310 of the medical database query system 400 including, for each user 310, an estimated current location of the user 310. The location database 600 is also configured to store information about a plurality of groups 312 of users 310 including, for each group 312, an estimated current location of the group 312.

In some embodiments, the location database 600 includes a calendar database, such as a Microsoft Outlook, Microsoft Exchange or Google Calendar database. The calendar database stores information about a plurality of meetings. For each meeting, the calendar database stores a location of the meeting, a time of the meeting and a list of participants in the meeting. Thus, calendar entries typically list participants (potential users 310) scheduled to meet together in a location. Often, calendar entries include titles or subjects, which may be parsed to infer an identity of the set of participants or purpose for meeting and, therefore, a group 312 identity. Thus, if the current user 310 is listed as a participant in a currently occurring meeting, together with other users 310 of a group 312 to which the current user 310 is a member, the user logon module 436 may infer that the current user 310 is currently a member of the group 312.

Optionally or alternatively, the location database 600 includes an electronic mail database configured to store a plurality of electronic messages. For each electronic message, the electronic mail database stores a subject and a list of recipients of the electronic message. In order to identify the group 312 associated with the current user 310, the user logon module 436 may automatically parse a distribution list of an electronic message. Recipients of an electronic message may be assumed to be members of a group 312.

Optionally or alternatively, the user logon module 436 may use both the calendar database and the electronic mail database to identify the group 312 to which the current user 310 is a member. The user logon module 436 may require both an electronic message and a calendar entry to identify the same group 312 before assuming the current user 310 is a member of the group. Further, the user logon module 436 may automatically parse subjects of electronic messages to find a plurality of electronic messages having a common or similar subject, and then concatenate distribution lists of the respective electronic messages. Optionally or alternatively, the user logon module 436 may automatically parse subjects of electronic messages to find subjects similar to calendar meeting titles or subjects to correlate electronic messages with meetings. Distribution lists of electronic messages that correlate with attendees at meetings, where the electronic messages and the meetings have common or similar subjects or titles, may be used to increase confidence that a proposed group 312 is, indeed, the group to which the user 310 is currently a member.

Thus, in order to identify the group associated with the user, the user logon module 436 may be configured to automatically parse a subject of an electronic message and/or automatically identify at least one recipient among the list of recipients of an electronic message.

If the user's 310 physical location can be independently estimated, i.e., apart from the user 310 being scheduled to attend a meeting, and the user 310 is determined to be located inside or within a predetermined distance of the conference room, the user 310 may be assumed to be meeting with others in the conference room and, therefore, to currently be a member of that group 312.

Calendar entries typically identify meeting places, such as by conference room name or other identifier. Since conference rooms typically are not mobile, the location database 600 can be provisioned with information about the physical location of each conference room. Then, as schematically illustrated in FIG. 6, if the user's 310 current physical location can be independently estimated, i.e., apart from the user 310 being scheduled to attend the meeting, such as from WiFi signals transmitted by a mobile device carried by the user 310, and the user 310 is determined to be located inside or within a predetermined distance of the conference room, the user 310 may be assumed to be meeting with the participants in the meeting room and, therefore, to currently be a member of that group 312. Optionally, the physical locations of others in a group 312 may be estimated independently, such as from respective WiFi signals transmitted by respective mobile devices carried by the other members of the group 312.

The location database 600 may be configured to store the estimated current location of the user 310, based on information from a wireless access point 602 to which a wireless mobile device, exemplified by a mobile telephone 604 or a Wi-Fi enabled laptop computer 606, that is registered to the user 310, is currently wirelessly connected 608. The wireless access point 602 may be a Wi-Fi access point, a cellular telephone base station or any other type of wireless infrastructure equipment capable of identifying and localizing the wireless mobile device 604-606. In the example shown in FIG. 6, the wireless access point 602 establishes the wireless connection 608 with the user's 310 wireless mobile device 604-606, due to its proximity to the wireless mobile device 604-606, compared to other wireless access points, exemplified by wireless access points 610 and 612, to which the user's 310 wireless mobile device 604-606 could, at least in theory, connect, but that are more distant.

Similarly, the location database 600 may be configured to store the estimated current locations of other users, represented by users 614, 616, 618 and 620, based on information from wireless access points 602, 610-612, to which respective wireless mobile devices (not shown) that are registered to the other users 614-620, are currently wirelessly connected. Users, for example users 614 and 616, that are proximate each other, as determined by the wireless access points 602, 610-612, may be assumed, for purposes of the location database 600, to be members of a group 312, or at least prospective members of a group 312, pending further clarification, such as by access to calendars and/or electronic messages of the prospective members of the group 312, as discussed herein.

If at least some users 310 are known to be members of a group 312, such as a result of provisioning of the location database 600 or provisioning of the database 424 (FIG. 4), then for purposes of the location database 600, any set of users 310 that are members of a given group 312 and are concurrently proximate each other, within a predetermined distance, may be deemed to be meeting together, for purposes of automatically determining if the current user 310 is proximate the meeting and, therefore, currently a member of the group 312.

Thus, the location database 600 may be configured to store the estimated current location of a group 312, based on information from at least one wireless access point 602, to which respective wireless mobile devices, that are registered to the users 614-616 associated with the group 312, are currently wirelessly connected.

Although automatically determining physical locations of respective users 310 has been discussed using wireless technology, wired computer network equipment may optionally or alternatively be used. For example, a wired router 622 may be used to estimate a location of a user 624 using a fixed-in-place computer 626 (or at least a fixed-in-place network connection), based on to which port on the router 622 the computer 626 establishes a network connection.

Thus, the user logon module 436 may compare the estimated current location of the user 310 to the estimated current location of at least one group 312 of a plurality of groups and identify the group 312 associated with the user 310, based on a match between the estimated current location of the user 310 and the estimated current location of the at least one group 312.

Figure 7:
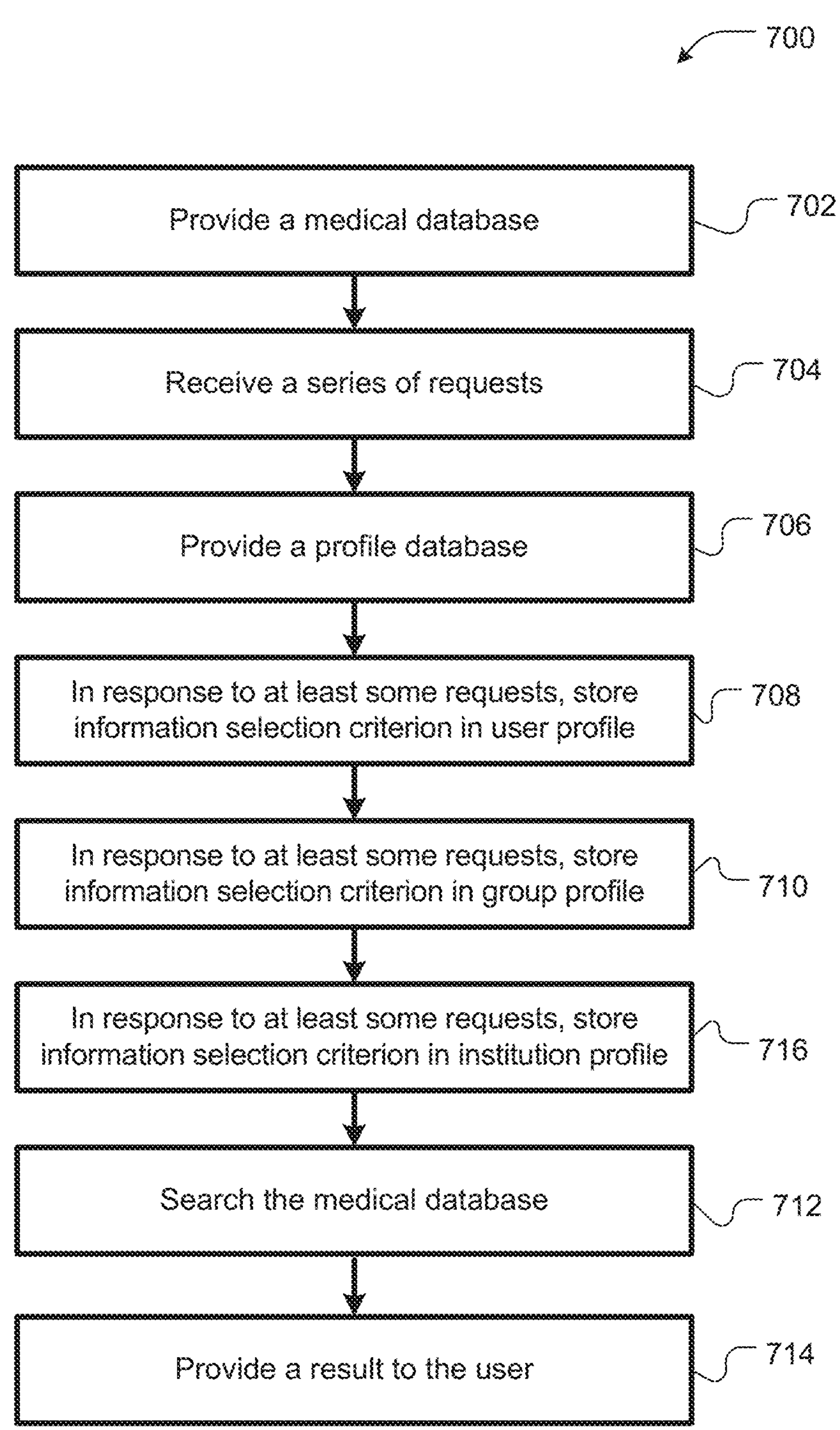
FIG. 7 is a flowchart schematically illustrating operations of the medical database query system of FIG. 4, according to an embodiment of the present invention.

FIG. 7 is a flowchart schematically illustrating operations of the medical database query system 300 implementing a method 700 for querying the medical database 306. The system 300 and method 700 are usable by a plurality of users 310. Each user 310 is associated with at least one group 312 of users 310.

At 702, a first database 306 is provided. The first database 306 is configured to store information about at least one of: (a) a plurality of medical devices 104, (b) a plurality of medical institutions 204 and (c) a plurality of patients 202. Each medical device 104 is configured for connection to a respective patient 202. The information about the medical institutions 204 includes information about medical institutions 204, at which respective ones of the patients 202 are currently admitted, and information about medical devices 104, to which respective ones of the patients 202 are currently connected. Each medical institution 204 is configured to admit patients 202 and house medical devices 104 configured for connection to respective patients 202.

At 704, a series of requests 404 is received from a user 310, via a human user interface 406-410. Each request is a request for information from the database 306. Each request includes a respective information selection criterion. In some embodiments, the human user interface includes a speech user interface, a graphical user interface and/or a text user interface.

At 706, a second database (profile database) 424 is provided. The second database 424 is configured to store, for each user 310, corresponding user profile information 418 and, for each group 312 of users 310, corresponding group profile information 420.

At 708, in response to at least some requests of the series of requests 404, the information selection criterion of each such request is stored into the second database 424, in association with the user 310 who made the at least some requests, thereby augmenting the user profile information 418 for the user 310.

At 710, in response to at least some requests of the series of requests 404, the information selection criterion of each such request is stored into the second database 424, in association with at least one group 312 associated with the user 310 who made the at least some requests, thereby augmenting the group profile information 420 for the at least one group 312.

At 712, the first database 306 is searched, based on a combination of: (a) an information selection criterion from a current request 412 of the series of requests 404, (b) at least one information selection criterion from the user profile information 418 corresponding to the user 310 who made the current request 412 and (c) at least one information selection criterion from the group profile information 420 corresponding to a group 312 associated with the user 310 who made the current request 412.

At 714, a result 500 is provided to the user 310, wherein the result 500 was returned as a result of the searching of the first database 306.

Optionally, each user 310 may be associated with an institution 204. In this case, the second database 424 is further configured to store, for each institution 204, corresponding institution profile information 422. Optionally at 716, in response to at least some requests of the series of requests 404, the information selection criterion of each request is stored into the second database 424, in association with the institution 204 associated with the user 310 who made the at least some requests, thereby augmenting the institution profile information 422 for the institution 204. In this case, at 712, the combination, upon which the first database 306 is searched, also includes: (d) at least one information selection criterion from the institution profile information 422 corresponding to an institution 204 associated with the user 310 who made the current request 412.

Figure 8:
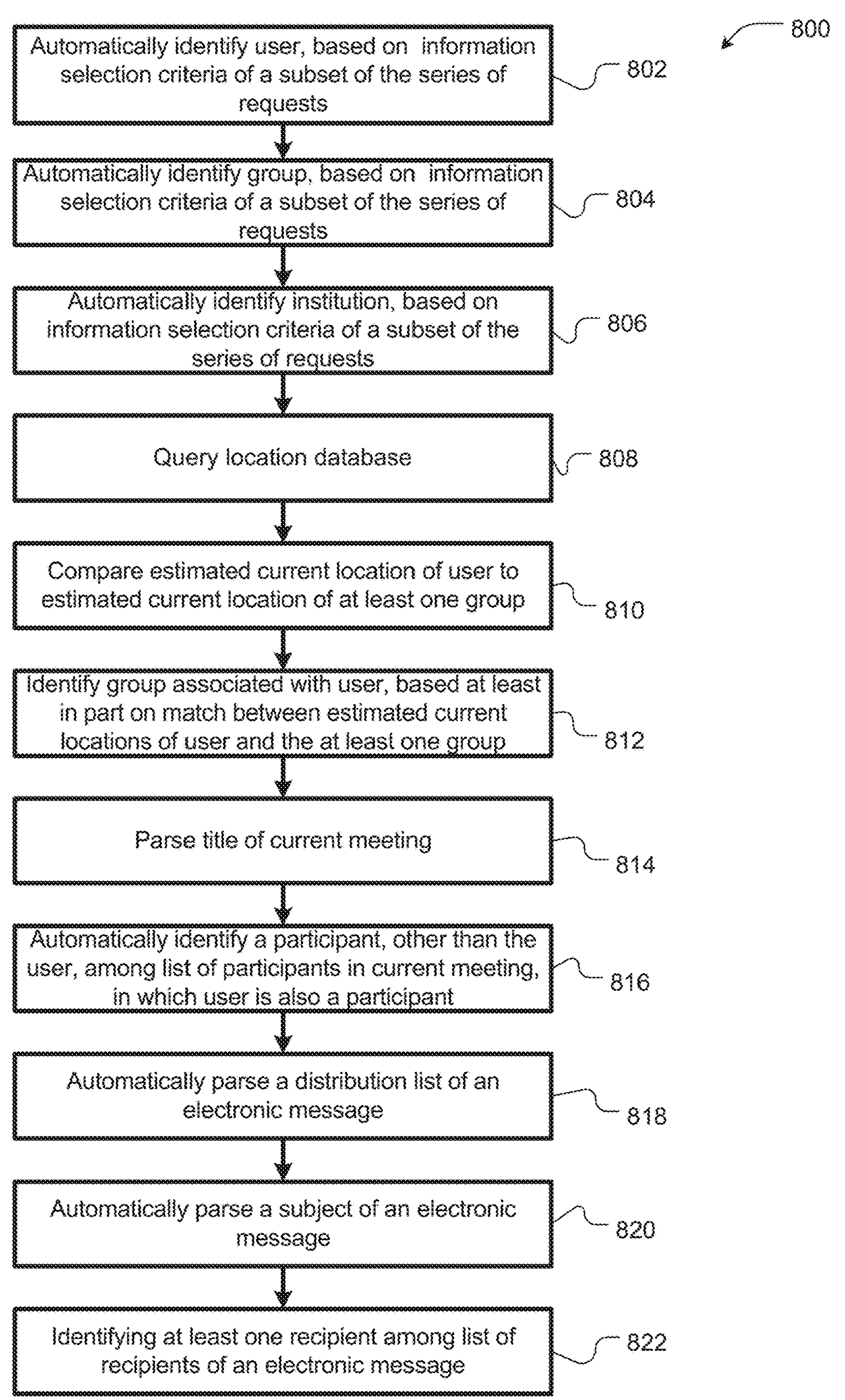
FIG. 8 is a flowchart schematically illustrating operations of an optional user logon module and location database of the medical database query system of FIGS. 4 and 5, according to respective embodiments of the present invention.

FIG. 8 is a flowchart schematically illustrating optional operations 800 of the optional user logon module 436 and the optional location database 600.

Optionally, at 802, the user 310 is automatically identified, based on the respective information selection criteria of a subset of the series of requests 404.

Optionally, at 804, the group 312 that is associated with the user 310 is automatically identified, based on the respective information selection criteria of a subset of the series of requests 404.

Optionally, at 806, the institution 204 associated with the user 310 is automatically identified, based on the respective information selection criteria of a subset of the series of requests 404.

Optionally, at 808, a third database (the location database) 600 is queried. The third database 600 is configured to store information about a plurality of users 310 and a plurality of groups 312. For each user, the third database 600 is configured to store an estimated current location of the user 310. For each group, the third database 600 is configured to store an estimated current location of the group 312. At 810, the estimated current location of the user 310 is compared to the estimated current location of at least one group 312 of the plurality of groups. At 812, the group 312 associated with the user 310 is identified, based at least in part on a match between the estimated current location of the user 310 and the estimated current location of the at least one group 312 of the plurality of groups.

As noted, the third database (location database) 600 may include a calendar database configured to store information about a plurality of meetings. For each meeting, the third database 600 stores a location of the meeting, a time of the meeting and a list of participants in the meeting.

Optionally, at 814, identifying the group 312 associated with the user 310 includes automatically parsing a title of a current meeting, of the plurality of meetings, in which the user 310 is a participant.

Optionally, at 816, identifying the group 312 associated with the user 310 includes automatically identify at least one participant, other than the user 310, among the list of participants in a current meeting, of the plurality of meetings, in which the user 310 is also a participant.

As noted, the third database (location database) 600 may include an electronic mail database configured to store a plurality of electronic messages including, for each electronic message, a subject and a list of recipients of the electronic message.

Optionally, at 818, identifying the group 312 associated with the user 310 includes automatically parsing a distribution list of an electronic message of the plurality of electronic messages.

Optionally, at 820, identifying the group 312 associated with the user 310 includes automatically parsing a subject of an electronic message of the plurality of electronic messages.

Optionally, at 822, identifying the group 312 associated with the user 310 includes identifying at least one recipient among the list of recipients of an electronic message of the plurality of electronic messages.

The third database (location database) 600 may be configured to store the estimated current location of the user 310, based on information from a wireless access point 602 to which a wireless mobile device 604-606, that is registered to the user 310, is currently wirelessly connected 608.

Optionally, the third database (location database) 600 is configured to store the estimated current location of the user 310, based on information from a wireless access point 602 to which a wireless mobile device 604-606, that is registered to the user 310, is currently wirelessly connected 608. In addition, the third database (location database) 600 may be configured to store the estimated current location of the group 312, based on information from at least one wireless access point 602 to which respective wireless mobile devices, that are registered to the respective users 614-616 associated with the group 312, are currently wirelessly connected.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The medical database query system 400, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combinations thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective databases from one another and are not intended to indicate any particular order or total number of databases in any particular embodiment. Thus, for example, a given embodiment may include only a second database and a third database.

The invention claimed is:

1. A system comprising one or more processors configured to:

receive, from a network access point, information regarding a device that has communicated with the network access point, wherein the device is registered to a user;

identify an institution associated with the user based on the information received from the network access point, wherein the identification of the institution associated with the user is further based on a match between an estimated current location of the user based on information from the network access point to which a wireless mobile device, that is registered to the user, is currently wirelessly connected, and an estimated current location of the identified institution;

receive, from the user, a request for information from a first database, wherein the received request comprises a first information selection criterion;

search the first database, based on a combination of: (a) the first information selection criterion, (b) a second information selection criterion retrieved from user profile information that is both stored in a second database and associated with the user, and (c) a third information selection criterion retrieved from institution profile information that is both stored in the second database and associated with the identified institution; and transmit, to the user, a result from the search of the first database.

2. The system of claim 1, wherein the user profile information comprises at least one information selection criterion from at least one previous request received from the user for information from the first database.

3. The system of claim 2, wherein the institution profile information comprises at least one information selection criterion from at least one previous request received from another user associated with the identified institution for information from the first database.

4. The system of claim 3, wherein the identified institution employs the user.

5. The system of claim 1, wherein the one or more processors are further configured to:

receive, from the user, a series of requests for information from the first database, wherein each one of the series of requests comprises a respective information selection criterion; and identify the user based on the respective information selection criteria of a subset of the series of requests.

6. The system of claim 5, wherein the identification of the institution associated with the user is further based on the respective information selection criteria of a subset of the series of requests.

7. The system of claim 1, wherein the one or more processors are further configured to: obtain the estimated current locations of the user and the identified institution from a calendar database, wherein the calendar database is configured to store information about a plurality of meetings.

8. The system of claim 1, wherein the one or more processors are further configured to: obtain the estimated current locations of the user and the identified institution from an electronic mail database, wherein the electronic mail database is configured to store a plurality of electronic messages.

9. The system of claim 1, wherein the current location of the user is estimated based on the information received from the network access point.

10. The system of claim 9, wherein the one or more processors are further configured to:

receive, from the network access point, additional information regarding another device that has communicated with the network access point, wherein the other device is registered to another user associated with the identified institution, and wherein the current location of the identified institution is estimated based on the additional information received from the network access point.

11. The system of claim 1, wherein the first database is a medical database configured to store information about a plurality of patients.

12. The system of claim 11, wherein the medical database is further configured to store information about a plurality of medical devices to which respective ones of the plurality of patients are currently connected.

13. The system of claim 12, wherein the transmitted result is a map of screens, and wherein each screen provides operational data for a respective one of the plurality of medical devices.

14. The system of claim 12, wherein the second information selection criterion comprises a name of one of the plurality of patients or a name of one of the plurality of medical devices.

15. The system of claim 12, wherein the third information selection criterion comprises a name of one of the plurality of patients or a name of one of the plurality of medical devices.

16. The system of claim 12, wherein the transmitted result comprises information about one of the plurality of patients or one of the plurality of medical devices.

17. The system of claim 1, wherein the transmitted result is a subset of the information in the first database corresponding to the first information selection criterion that is further limited by the second information selection criterion and the third information selection criterion.

18. A method comprising:

receive, with one or more processors, from a network access point, information regarding a device that has communicated with the network access point, wherein the device is registered to a user;

identify, with the one or more processors, an institution associated with the user based on the information received from the network access point, wherein the identification of the institution associated with the user is further based on a match between an estimated current location of the user based on information from the network access point to which a wireless mobile device, that is registered to the user, is currently wirelessly connected, and an estimated current location of the identified institution;

receiving, with the one or more processors, from the user, a request for information from a first database, wherein the received request comprises a first information selection criterion;

searching, with the one or more processors, the first database, based on a combination of: (a) the first information selection criterion, (b) a second information selection criterion retrieved from user profile information that is both stored in a second database and associated with the user, and (c) a third information selection criterion retrieved from institution profile information that is both stored in the second database and associated with the identified institution; and transmitting, with the one or more processors, to the user, a result from the search of the first database.

19. A non-transitory computer-readable medium having instructions stored thereon that, when executed by one or more processors, cause the one or more processors to:

receive, from a network access point, information regarding a device that has communicated with the network access point, wherein the device is registered to a user;

identify an institution associated with the user based on the information received from the network access point, wherein the identification of the institution associated with the user is further based on a match between an estimated current location of the user based on information from the network access point to which a wireless mobile device, that is registered to the user, is currently wirelessly connected, and an estimated current location of the identified institution;

receive, from the user, a request for information from a first database, wherein the received request comprises a first information selection criterion;

search the first database, based on a combination of: (a) the first information selection criterion, (b) a second information selection criterion retrieved from user profile information that is both stored in a second database and associated with the user, and (c) a third information selection criterion retrieved from institution profile information that is both stored in the second database and associated with the identified institution; and transmit, to the user, a result from the search of the first database.

* * * * *